(12) United States Patent
Cook et al.

(10) Patent No.: US 9,968,391 B2
(45) Date of Patent: May 15, 2018

(54) FACET SCREWS

(71) Applicant: Fellowship of Orthopaedic Researchers, Inc., Metairie, LA (US)

(72) Inventors: Stephen D. Cook, New Orleans, LA (US); Shoib Bajaj, Kenner, LA (US)

(73) Assignee: Fellowship of Orthopaedic Researchers, LLC, Metairie, LA (US)

( * ) Notice: Subject to any disclaimer, the term of this patent is extended or adjusted under 35 U.S.C. 154(b) by 745 days.

(21) Appl. No.: 14/075,896

(22) Filed: Nov. 8, 2013

(65) Prior Publication Data

US 2014/0135851 A1 May 15, 2014

Related U.S. Application Data

(60) Provisional application No. 61/724,558, filed on Nov. 9, 2012.

(51) Int. Cl.
*A61B 17/86* (2006.01)
*A61B 17/70* (2006.01)

(52) U.S. Cl.
CPC ............ *A61B 17/863* (2013.01); *A61B 17/70* (2013.01); *A61B 17/8605* (2013.01)

(58) Field of Classification Search
CPC ............ A61B 17/8605; A61B 17/8625; A61B 17/863; A61B 17/8635; A61B 17/864; A61B 17/86; A61B 17/866
See application file for complete search history.

(56) References Cited

U.S. PATENT DOCUMENTS

| 5,098,435 | A | * | 3/1992 | Stednitz | A61B 17/1637 411/387.5 |
| 5,536,127 | A | * | 7/1996 | Pennig | A61B 17/863 411/397 |
| 5,544,993 | A | * | 8/1996 | Harle | B23G 5/04 411/411 |
| 6,030,162 | A | * | 2/2000 | Huebner | A61B 17/1682 411/263 |
| 9,011,505 | B2 | * | 4/2015 | Prandi | A61B 17/863 411/387.8 |
| 9,161,793 | B2 | * | 10/2015 | Huebner | A61B 17/863 |

* cited by examiner

*Primary Examiner* — Anu Ramana
(74) *Attorney, Agent, or Firm* — Haug Partners LLP

(57) ABSTRACT

Facet screws comprise a lower portion have lower threads that have a constant outer or major diameter. The lower portion of the facet screws can also have a tapered or conical shape in a direction toward the lower end, and relative to a longitudinal axis, of the facet screw. Therefore, the lower threads closest to the lower end have a greater surface area for engaging the bone of a patient as compared to the lower threads furthest away from the lower end, i.e., closest to the top of the lower threads. One or more of the lower threads also can include certain dimensions and shapes that facilitate insertion and retention of the facet screws in the bone of a patient.

15 Claims, 5 Drawing Sheets

FACET SCREWS

CROSS REFERENCE TO RELATED APPLICATIONS

This application claims priority to, and the benefit of, U.S. Provisional Patent Application Ser. No. 61/724,558 filed Nov. 9, 2012, which is incorporated herein by reference.

FIELD OF THE INVENTION

The invention is directed to fasteners and, in particular, to facet screws for securing to a bone in an animal.

BACKGROUND

In general, facet screws include a shaft having a lower end, an upper end, and a plurality of threads disposed along an outer wall surface of at least a portion of the shaft. The upper end includes a profile to receive a tool, such as a screw driver, to rotate the shaft and cause it to rotate into the bone.

SUMMARY OF INVENTION

The present invention is directed to facet screws for securing into bone. The facet screws of the present invention may comprise a shaft with a first end (hereinafter "upper end") and a second end (hereinafter "lower end"). The facet screws may also comprise a portion of the shaft at or near the upper end (hereinafter "upper portion") and a portion of the shaft at or near the lower end (hereinafter "lower portion"). In certain embodiments, the facet screws may be secured to the bone in the direction of the lower end.

In some embodiments, the upper portion may comprise threads (hereinafter "upper threads"), and in certain embodiments, the lower portion may comprise threads (hereinafter "lower threads"). In particular embodiments, the lower threads may have a constant or near-constant outer or major diameter.

All or a section of the lower portion may also have a tapered or conical shape in the direction of the lower end of the facet screw. Therefore, the lower threads closest to the lower end have a greater surface area for engaging the bone of a patient as compared to the lower threads furthest away from the lower end, i.e., lower threads closest to the upper end.

In certain embodiments, one or more of the lower threads may comprise certain dimensions and shapes that facilitate insertion and retention of the facet screws in the bone of an animal. It is to be understood, however, that the effects and results of the facet screws disclosed herein are dependent, at least in part, upon the skill and training of the operators and surgeons.

BRIEF DESCRIPTION OF DRAWINGS

Understanding of the present invention will be facilitated by consideration of the following detailed description of the embodiments of the present invention taken in conjunction with the accompanying drawings, in which like numerals refer to like parts and in which.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The facet screws of the present invention may comprise an upper end, an upper portion with upper threads, a lower end, and a lower portion with lower threads. In certain embodiments, the upper threads may comprise cylindrical threading (along the vertical or length of the screw) and the lower threads may comprise conical threading (along the vertical or length of the screw).

In some embodiments, the cylindrical threading of the upper portion may engage with, affix to, or otherwise be disposed in a cortical bone region of a facet joint of a human or animal. In certain embodiments, the conical threading of the lower portion may engage with, affix to, or otherwise be disposed in a cancellous bone region of a facet joint of a human or animal. Without wishing to be bound by the theory, it is believed that the cancellous bone region is less dense than the cortical bone region within the facet joint and the larger/deeper threading of the conical threaded portion may enhance or increase the pullout force of the facet screw from its inserted position within a human or animal. Further without wishing to be bound by the theory, the conical thread design may not compromise mechanical strength of the screw because conical threading is in the lower portion of the facet screw and the greatest loads may be carried by the upper portion of the screw with the cylindrical geometry that has a larger core diameter for greater mechanical strength. In addition, also without wishing to be bound by the theory, the use of different thread pitches for the cylindrical and conical screw thread portions of the screw may allow compression of the joint surfaces as the screw is inserted in a human or animal to aid the fusion process.

Thus, it is believed that the facet screws of the present invention may have an enhanced or increased "pullout force" as compared to a conventional facet screw having a cylindrical lower or minor diameter along the lower portion of the shaft of the facet screw. In particular, the facet screws having a conically-shaped or tapered lower portion may have at least about a 1% and as great as about a 30% enhanced or increased "pullout force" as compared to conventional cylindrically-shaped facet screws.

Figure 1:
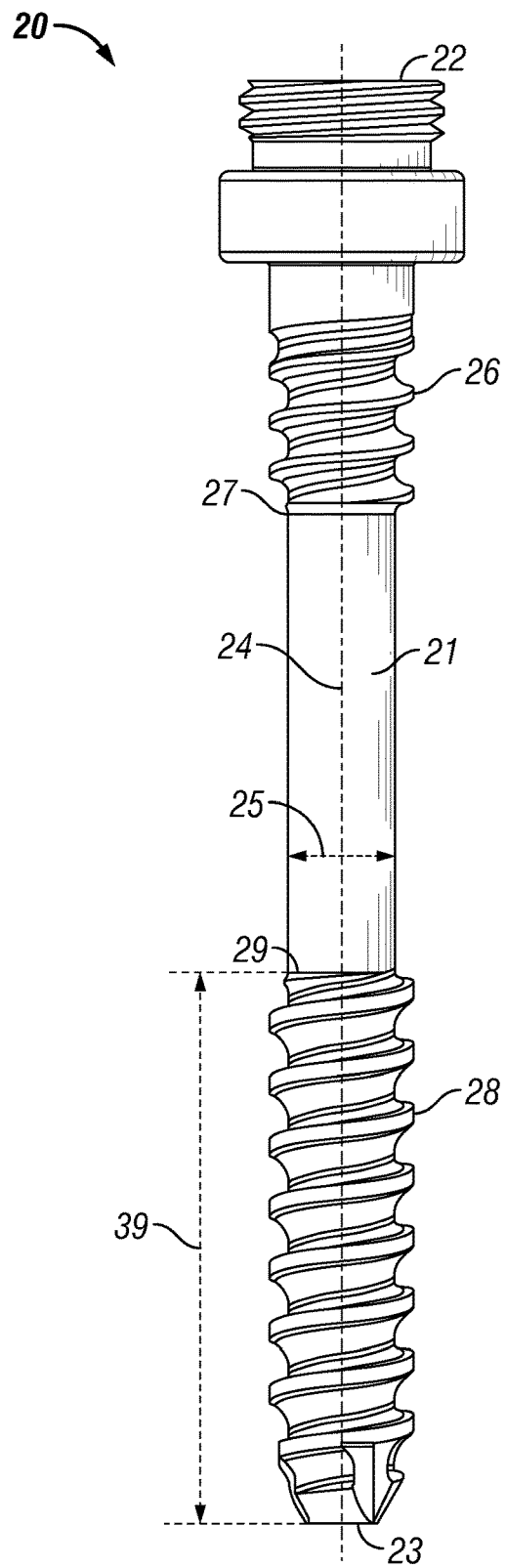
FIG. 1 is a perspective view of one embodiment of a facet screw of the present invention.
Figure 2:
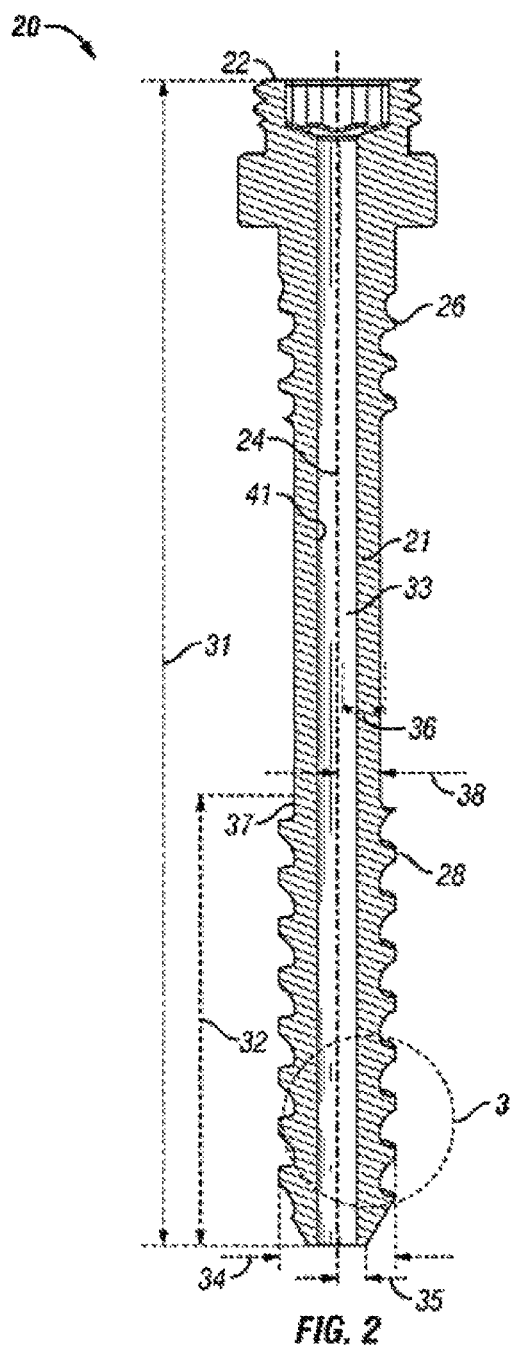
FIG. 2 is a cross-sectional view of the facet screw shown in FIG. 1.

Referring now to FIGS. 1 and 2, in certain embodiments, facet screw 20 includes shaft 21 having upper end 22, lower end 23, longitudinal axis 24, and shaft or minor outer diameter 25. Upper threads 26 may be disposed in upper portion 27 at or near the upper end 22 and lower threads 28 may be disposed in lower portion 29 at or near lower end 23. Screw 20 may include length 31 measured from upper end 22 to lower end 23. Lower thread length 32 may be measured from lower end 23 to the top of lower threads 28. Longitudinal bore 33 may be disposed through shaft 21 from upper end 22 to lower end 23. Lower threads 28 may define lower thread or major outer diameter 34 (shown in FIG. 2) which may be constant.

Outer wall surface 37 of lower portion 29 of shaft 21 may be tapered or conically shaped as it approaches lower end 23. In certain embodiments, the tapering of outer wall surface 37 may begin at, or slightly above, the top or uppermost point of lower threads 28. As a result, the thickness of the wall of shaft 21 defined by outer wall surface 37 and inner wall surface 41 (FIGS. 2 and 3) of bore 33 within lower portion 29 may lessen as it approaches lower end 23. As noted above, however, lower thread or major outer diameter 34 may remain constant. Therefore, the lower threads 28 closest to lower end 23 may have a greater surface area for engaging the bone of an animal as compared to the lower threads 28 furthest away from lower end 23, i.e., closest to the top of lower threads 28.

Angle 36, as shown in FIG. 2, defines the degree of tapering of outer wall surface 37 toward lower end 23. In certain embodiments, angle 36 may be in the range from about 0.5 degree to about 2 degrees. In some embodiments, angle 36 may be in the range from about 1.0 degrees to about 1.5 degrees. In particular embodiments, angle 36 may be in the range from about 1.2 degrees to about 1.3 degrees.

The tapering of lower portion 29 is also shown in FIG. 2 as defined by distance 35 and distance 38. Distance 38 is measured from axis 24 to outer wall surface 37 at the uppermost point of lower threads 28, i.e., about the point at which downward tapering of outer wall surface 37 begins. Distance 35 is measured from axis 24 to outer wall surface 37 at lower end 23. In some embodiments, distance 38 may be about 0.05 to about 0.07 inches, such as about 0.065 inches, and distance 35 may be about 0.04 to about 0.06 inches, such as about 0.050 inches. In certain embodiments, distance 38 may be approximately 0.0650000 inches and distance 35 may be approximately 0.0500000 inches. In some embodiments, thread length 32 can be about 0.5 to about 0.8 inches, such as about 0.684 inches, and bore 33 can be about 0.04 to about 0.07 inches, such as about a constant 0.059 inches; as a result, angle 36 may be defined by a right triangle having a height of about 0.01 to about 0.03 inches, such as about 0.015 inches, a base of about 0.5 to about 0.8 inches, such as about 0.684 inches, and a hypotenuse of about 0.5001 to about 0.8006 inches, to be about 1.1 to about 1.4 degrees, or about 1.27 degrees. In certain embodiments, thread length 32 can be approximately 0.6840000 inches and bore 33 can be a constant 0.0590000 inches such that angle 36 may be defined by a right triangle having a height of approximately 0.0150000 inches, a base of approximately 0.6840000 inches, and a hypotenuse of approximately 0.6841644 inches to be approximately 1.27 degrees.

Figure 4:
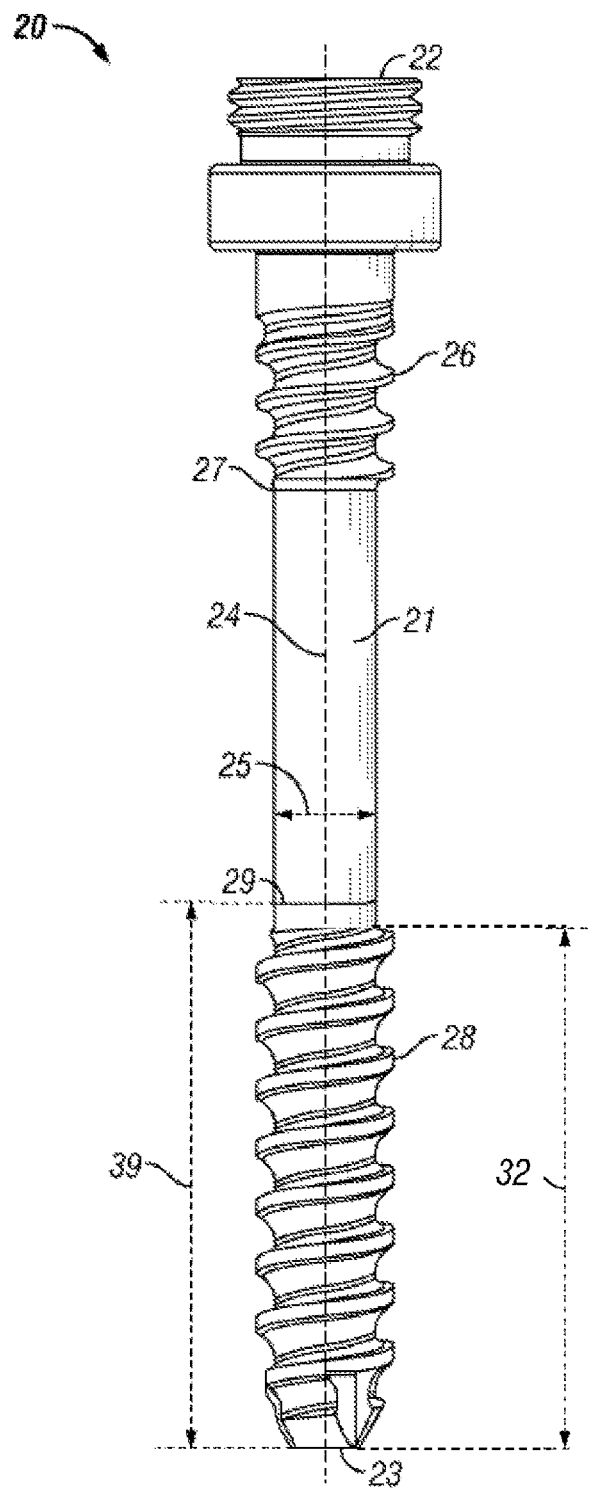
FIG. 4 is a perspective view of one embodiment of a facet screw of the present invention.
Figure 5:
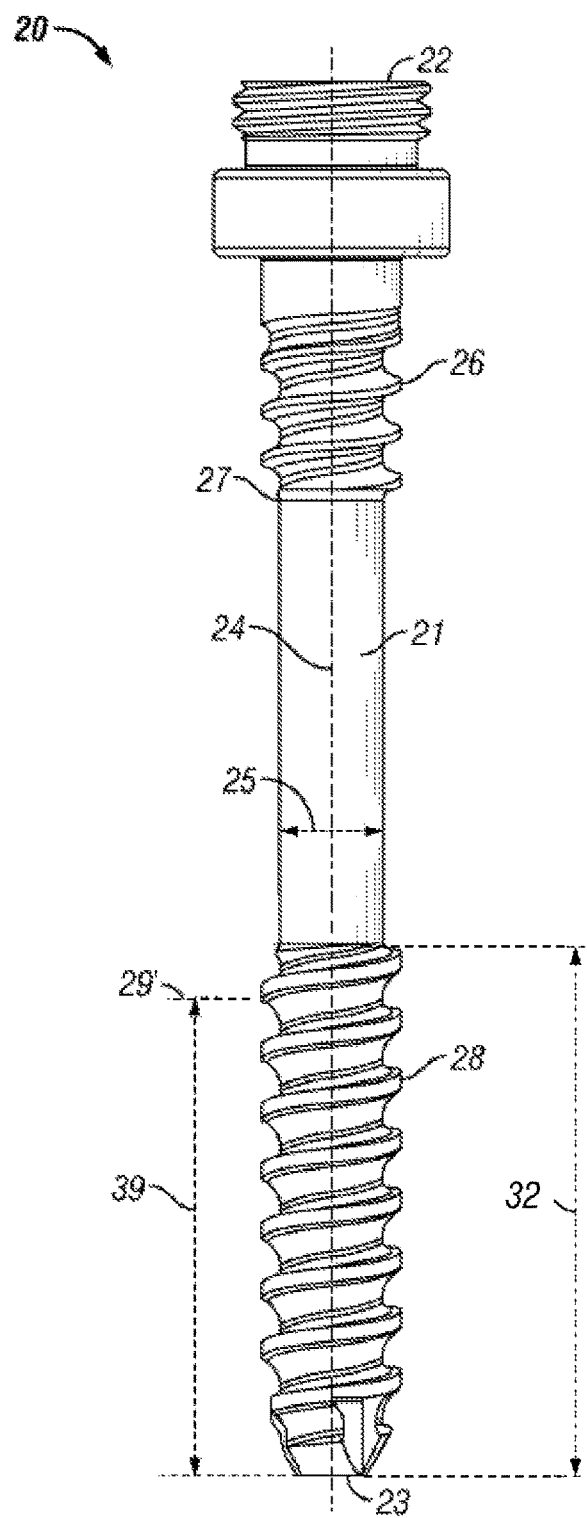
FIG. 5 is a perspective view of one embodiment of a facet screw of the present invention.

In certain embodiments, length 39 of lower portion 29 may be equal to thread length 32. It is to be understood, however, not all of lower portion 29 may be required to be tapered. Further, length 39 of lower portion 29 can be longer than thread length 32 (see FIG. 4). Alternatively, length 39 may be shorter than thread length 32 (see FIG. 5).

Figure 3:
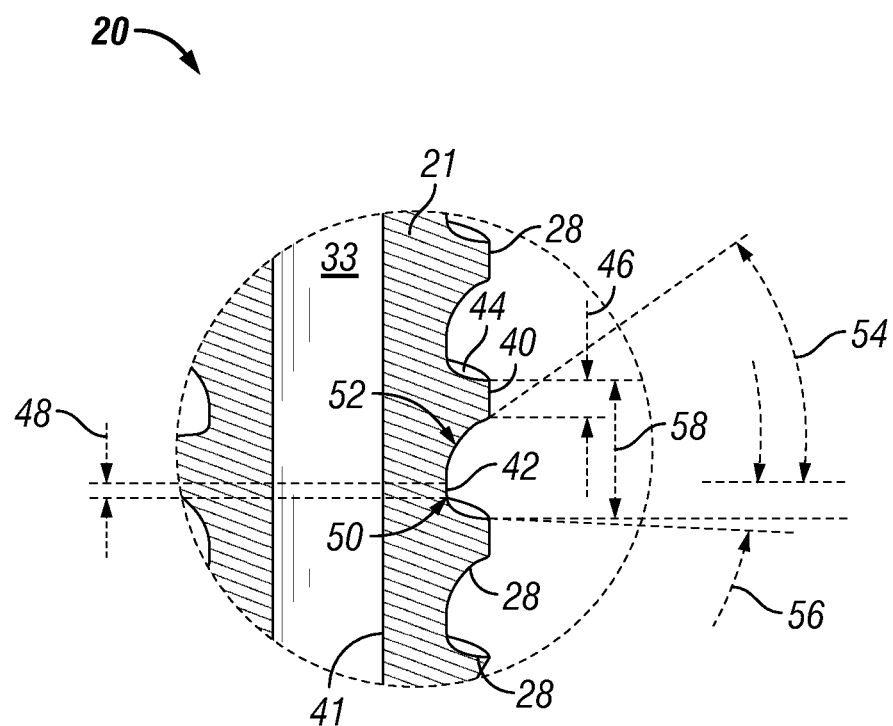
FIG. 3 is a partial cross-sectional view of a portion of the facet screw shown in FIG. 2, taken along line 3-3.

Referring now to FIG. 3, lower threads 28 may have certain shapes and dimensions. As shown in FIG. 3, lower threads 28 may comprise thread outer wall surface 40, thread inner wall surface 42, and thread top wall surface 44. Thread outer wall surface 40 may have portion 46 that is substantially parallel to inner wall surface 41 of bore 33; and thread inner wall surface 42 may have portion 48 that is substantially parallel to inner wall surface 41 of bore 33.

Thread inner wall surface 42 may be connected to thread top wall surface 44 by radius of curvature 50; and may be connected to thread outer wall surface 40 by radius of curvature 52.

Each of lower threads 28 may comprise upward angle 54 and downward angle 56 to facilitate insertion of facet screw 20 into a substrate such as bone. Distance 58 defines the measurement between thread top wall surfaces 44 of adjacent lower threads 28.

In some embodiments, portion 46 may be in the range from about 0.006 inches to about 0.014 inches; portion 48 may be in the range from about 0.003 inches to about 0.02 inches; radius of curvature 50 may be in the range from about 0.007 inches to about 0.02 inches; radius of curvature 52 may be in the range from about 0.03 inches to about 0.05 inches; upward angle 54 may be in the range from about 30 degrees to about 40 degrees; downward angle 56 may be in the range from about 1 degree to about 5 degrees; and distance 58 may be in the range from about 0.06 inches to about 0.09 inches. In certain embodiments, portion 46 may be in the range from approximately 0.0075 inches to approximately 0.0125 inches; portion 48 may be in the range from approximately 0.0040 inches to approximately 0.0100 inches; radius of curvature 50 may be in the range from approximately 0.0080 inches to approximately 0.0160 inches; radius of curvature 52 may be in the range from approximately 0.0350 inches to approximately 0.0400 inches; upward angle 54 may be in the range from approximately 30 degrees to approximately 40 degrees; downward angle 56 may be in the range from approximately 1 degrees to approximately 5 degrees; and distance 58 may be in the range from approximately 0.0700 inches to approximately 0.0800 inches.

In further embodiments, portion 46 may be about 0.011 inches; portion 48 may be about 0.007 inches; radius of curvature 50 may be about 0.012 inches; radius of curvature 52 may be about 0.039 inches; upward angle 54 may be about 35 degrees; downward angle 56 may be about 3 degrees; and distance 58 may be about 0.076 inches. In particular embodiments, portion 46 may be approximately 0.0110 inches; portion 48 may be approximately 0.0070 inches; radius of curvature 50 may be approximately 0.0120 inches; radius of curvature 52 may be approximately 0.0390 inches; upward angle 54 may be approximately 35 degrees; downward angle 56 may be approximately 3 degrees; and distance 58 may be approximately 0.0760 inches.

In certain embodiments, facet screw 20 may be made of a number of suitable materials, including metal and non-metal materials with and without various coatings. For example, facet screw 20 may be made of a resorbable polymer such as a polylactic acid (PLA)/polyglycolic acid (PGA) type material. Without wishing to be bound by the theory, it is believed that such resorbable material may "go away" after the fusion process occurs and could eliminate long term problems related to facet screw 20 being present. Such problems may biomechanical (stress shielding the bone due to its rigidity being greater than the bone) and/or biomaterial, in that the metal materials corrode and release ions and debris and may cause tissue reactions to metal debris and corrosion and metal ion release. Other suitable materials can include non-resorbable polymers such as polyether ether ketone (PEEK) materials. Without wishing to be bound by the theory, it is believed that non-resorbable materials may be stiffer similar to bone, which may help prevent stress shielding of the bone aiding the fusion process and helping to maintain the bone by having it stressed more physiologically in the long term.

In still further embodiments, facet screw 20 may be coated with a ceramic material such as hydroxyapatite, which may have the benefit of a biologically more favorable surface through the release of calcium and phosphate to the surrounding tissues due to slow dissolution. The release of these materials may aid in the biological fusion process. In addition, ceramic coatings may seal off the metal and reduce ion release and corrosion. Still other coatings such as titanium nitrides and chromium carbides may be used for better corrosion protection and reduction of metal ion release.

TESTING AND EXAMPLES

The axial pullout strength of facet screws (per American Society for Testing and Materials (ASTM) F543-07) were tested and compared. In summary, the mean pullout failure load of the conical facet screw (957 ±45 N) was 11% greater than the mean failure load of the cylindrical facet screw (848±22 N).

Materials and Methods

Two screw variations were tested in axial pullout. The screw name reflected the distal minor diameter feature of each screw. The cylindrical screw had a constant minor diameter, which is in contrast to a conical screw such as those of the embodiments of FIGS. 1-3, which had a variable, i.e., tapered or conically-shaped, distal minor diameter. Table 1 outlines the size and length of each screw as well as the pilot hole diameter used for each screw.

TABLE 1

Screw Description and Pilot Hole Diameter

| Screw Design | Major Diameter (mm) | Minor Diameter (mm) | Length (mm) | Pilot Hole Ø (mm) | Number of Pullouts |
|---|---|---|---|---|---|
| Cylindrical | 4.5 | 3.4 | 45 | 3.1 | 3 |
| Conical | 4.5 | 2.5-3.4* | 45 | 2.8 | 3 |

*Minor diameter ranged from 2.5 mm, at the screw tip, to 3.4 mm at the beginning of the distal or lower threads.

One cylindrical screw and one conical screw were tested per block (#20 pcf solid rigid polyurethane foam per ASTM F 1839-01; 55 mm×25 mm×40 mm). The pilot holes were drilled 20 mm apart from each other, perpendicular to the top surface of the block and aligned with the rise of the foam. Only the distal or lower threads of the screws were pull-out tested.

At the beginning of each test, a test block was inserted under the grip plate (grip span=32.5 mm) and each screw was pulled at a rate of 5 mm/min until failure.

Results

Table 2 lists the mean failure load of all the screws tested in axial pullout. The mean failure load of the cylindrical and conical facet screws was 848±22 N and 957±45 N respectively.

TABLE 2

Mean Failure Load of the Cylindrical and Conical Facet Screws.

| n | Cylindrical | Conical |
|---|---|---|
| 1 | 833N | 1005N |
| 2 | 873N | 950N |
| 3 | 837N | 916N |
| Mean | 848N | 957N |
| Std. Dev. | 22N | 45N |

Those of ordinary skill in the art will recognize that many modifications and variations of the present invention may be implemented without departing from the spirit or scope of the invention. It is to be understood that the invention is not limited to the exact details of construction, operation, exact materials, or embodiments shown and described, as modifications and equivalents will be apparent to one skilled in the art. Thus, it is intended that the present invention cover the modification and variations of this invention provided they come within the scope of the appended claims and their equivalents.

What is claimed is:

1. A facet screw comprising:
a shaft having an upper end, a lower end, a longitudinal axis, an outer wall surface, and a bore defining an inner wall surface, wherein a portion of the shaft at the lower end defines a lower portion; and
a plurality of threads disposed along the outer wall surface toward the lower end,
wherein the outer wall surface of the lower portion has a conical cross-section in a direction toward the lower end and relative to the longitudinal axis of the shaft;
wherein the outer wall surface of the lower portion having the conical cross-section defines a length relative to the longitudinal axis;
wherein the plurality of threads disposed along the outer wall surface toward the lower end define a thread outer wall diameter;
wherein the plurality of threads defines a thread length, wherein the thread length is the length relative to the longitudinal axis between an upper most thread of the plurality of threads and a lower most thread of the plurality of threads; and
wherein the thread outer wall diameter is constant along a portion of the outer wall surface on which the plurality of threads is disposed; and
wherein at least part of the portion of the outer wall surface in which the thread outer wall diameter is constant overlaps with at least part of the outer wall surface of the lower portion having the conical cross-section.

2. The facet screw of claim 1, wherein at least one of the plurality of threads defines an upward angle in the range from about 30 degrees to about 40 degrees.

3. The facet screw of claim 2, wherein at least one of the plurality of threads defines a downward angle in the range from about 1 degree to about 5 degrees.

4. The facet screw of claim 1, wherein at least one of the plurality of threads defines a thread outer wall surface, a thread inner wall surface, and a thread top wall surface, the thread top wall surface of one of the plurality of threads and the top thread wall surface of another of the plurality of threads defining a distance,
wherein the thread outer wall surface includes an outer wall surface portion that is substantially parallel to the longitudinal axis and the thread inner wall surface includes an inner wall surface portion that is substantially parallel to the longitudinal axis, and
wherein the thread inner wall surface is connected to the thread top wall surface by a first radius of curvature and the thread outer wall surface is connected to the thread inner wall surface by a second radius of curvature.

5. The facet screw of claim 4, wherein
the thread outer wall surface portion is about 0.006 inches to about 0.014 inches in length relative to the longitudinal axis, the thread inner wall surface portion is about 0.003 inches to about 0.02 inches in length relative to the longitudinal axis, the first radius of curvature is in the range from about 0.007 inches to about 0.02 inches, the second radius of curvature is in the range from about 0.03 inches to about 0.05 inches, and the distance between two of the plurality of threads is in the range from about 0.06 inches to about 0.09 inches.

6. The facet screw of claim 5, wherein the first radius of curvature partially defines a downward angle in the range from about 30 degrees to about 40 degrees, and the second radius of curvature partially defines a downward angle in the range from about 1 degree to about 5 degrees.

7. The facet screw of claim 6, wherein the thread outer wall surface portion is about 0.011 inches in length relative to the longitudinal axis, the thread inner wall surface portion is about 0.007 inches in length relative to the longitudinal axis, the first radius of curvature is about 0.012 inches, the second radius of curvature is about 0.039 inches, the distance between two of the plurality of threads is about 0.076 inches, the upward angle is about 35 degrees, and the downward angle is about 3 degrees.

8. The facet screw of claim 1, wherein each of the plurality of threads defines a thread outer wall surface, a thread inner wall surface, a thread top wall surface, an upward angle, and a downward angle, wherein the thread outer wall surface of each of the plurality of threads includes an outer wall surface portion that is substantially parallel to the longitudinal axis and the thread inner wall surface of each of the plurality of threads includes an inner wall surface portion that is substantially parallel to the longitudinal axis, and wherein the thread inner wall surface of each of the plurality of threads is connected to the thread top wall surface by a first radius of curvature, the first radius of curvature partially defining the downward angle, and the thread outer wall surface of each of the plurality of threads is connected to the thread inner wall surface by a second radius of curvature, the second radius of curvature partially defining the upward angle.

9. The facet screw of claim 8, wherein the thread outer wall surface portions of each of the plurality of threads is about 0.006 inches to about 0.014 inches in length relative to the longitudinal axis, the thread inner wall surface portions of each of the plurality of threads is about 0.003 inches to about 0.02 inches in length relative to the longitudinal axis, the first radii of curvature of each of the plurality of threads is in the range from about 0.007 inches to about 0.02 inches, the second radii of curvature of each of the plurality of threads is in the range from about 0.03 inches to about 0.05 inches, the downward angles of each of the plurality of threads is in the range from about 30 degrees to about 40 degrees, and the upward angles of each of the plurality of threads are in the range from about 1 degree to about 5 degrees.

10. The facet screw of claim 9, wherein the thread outer wall surface portions of each of the plurality of threads is about 0.011 inches in length relative to the longitudinal axis, the thread inner wall surface portions of each of the plurality of threads is about 0.007 inches in length relative to the longitudinal axis, the first radii of curvature of each of the plurality of threads is about 0.012 inches, the second radii of curvature of each of the plurality of threads is about 0.039 inches, the upward angles of each of the plurality of threads is about 35 degrees, and the downward angle of each of the plurality of threads is about 3 degrees.

11. The facet screw of claim 9, wherein a pair of adjacent threads of the plurality of threads defines a distance measured from the outer edge of the thread top surface of one of pair of adjacent threads to the outer edge of the thread top surface of the other of the pair of adjacent threads, the distance being in the range from about 0.07 inches to about 0.08 inches.

12. The facet screw of claim 11, wherein the distance is about 0.076 inches.

13. The facet screw of claim 1, wherein the length defined by the outer wall surface of the lower portion having the conical cross-section is equal to the thread length.

14. The facet screw of claim 1, wherein the length defined by the outer wall surface of the lower portion having the conical cross-section is greater than the thread length.

15. The facet screw of claim 1, wherein the length defined by the outer wall surface of the lower portion having the conical cross-section is less than the thread length.

* * * * *